United States Patent [19]

Siri

[11] Patent Number: Plant 5,304

[45] Date of Patent: Oct. 23, 1984

[54] MINIATURE CARNATION

[75] Inventor: Angelo J. Siri, San Francisco, Calif.

[73] Assignee: Siri Brothers Nursery, Inc., East Palo Alto, Calif.

[21] Appl. No.: 397,117

[22] Filed: Jul. 12, 1982

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Limbach, Limbach & Sutton

[57] ABSTRACT

A miniature carnation characterized by its rapid growth and white blossoms born on well branched stems.

4 Drawing Figures

BACKGROUND OF THE NEW PLANT

This invention comprises a new and distinct miniature carnation variety that has its own set of characteritics that set it apart from all other varieties of miniature carnations. The newly discovered variety, called "Snowflake," originated as a sport of Niky, an unpatented variety.

The botanical clasification of the new variety is *Dianthus caryophyllus Longicaulis.* The commercial classification is Miniature Carnation. The plant takes the form of a bush.

Asexual propagation of the newly discovered miniature carnation variety has been made at Siri Brothers Nursery, Inc. at East Palo Alto, Calif. by taking cuttings. The cuttings so taken and grown, have consistently produced flowers that have the new and distinct characteristics hereinafter described.

DECRIPTION OF THE DRAWINGS

This new variety of miniature carnation plant is illustrated by the accompanying drawings which show the color characteristics of the flower as nearly true as it is resonably possible to obtain through conventional photographic procedures.

DESCRIPTION OF THE NEW PLANT

Figure 1:
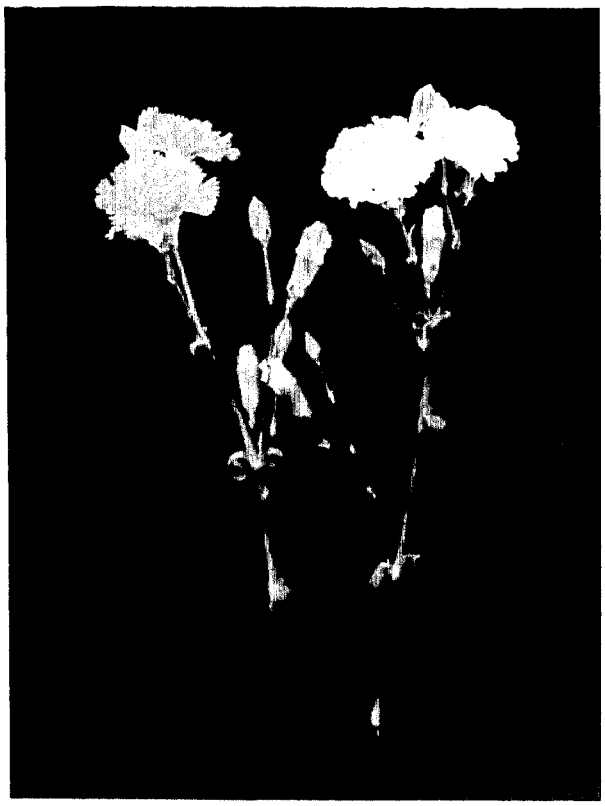
FIG. 1. PRIOR ART
FIG. 1 shows sprays and stems of the new variety Snowflake on the right and the piror Niky on the left.
Figure 2:
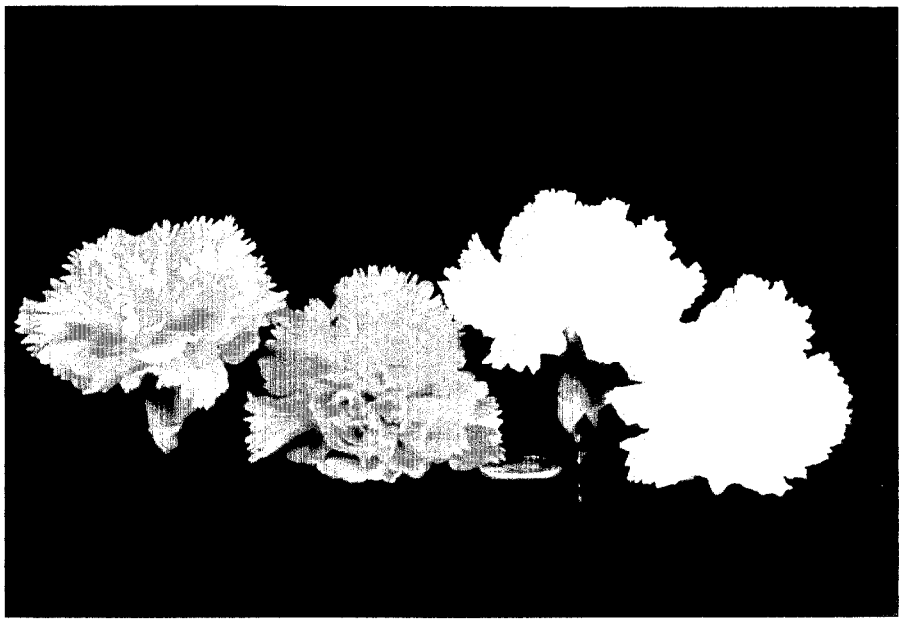
FIG. 2 shows the blooms of the new variety Snowflake on the right and the prior Niky on the left.
Figure 3:
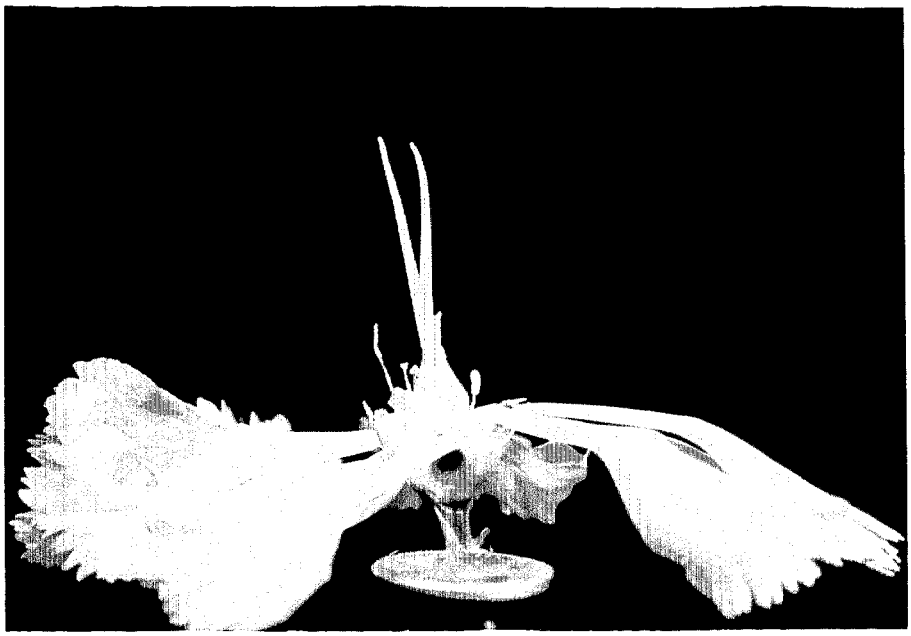
FIG. 3. PRIOR ART
FIG. 3 shows the interior of the prior Niky.
Figure 4:
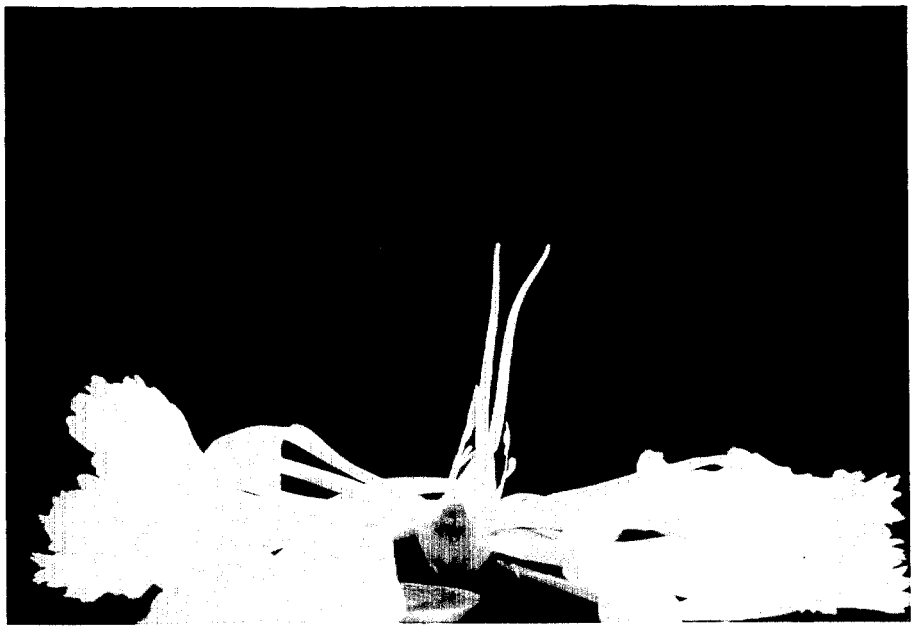
FIG. 4 shows the interior of the new variety Snowflake.

The following detailed description of the new variety is based on my detailed observations of the new cultivar which were made at Siri Brothers Nursery Inc. at 940 O'Connor Street, East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore Md. and "R.H.S." for Royal Horticultural Colour Chart, The Royal Horticultural Society, London England.

GROWTH HABITS

Height: Average.

Foliage: Average.

Speed of growth: Exceptionally fast.

Root system: Average.

FOLIAGE

Leaf size:

*Length.*—Average length 4½ inches at mid-stem.

*Width.*—Averages ⅜ inches at mid-stem.

Leaf shape: Average curl with a long acuminating tip.

Leaf texture: Smooth and leathery.

Leaf color;

*Upperside.*—R.H.S. Green Group 139A with a whitish color over the green.

*Underside.*—R.H.S. Green Group 139A with a whitish color over the green.

Leaf ribs: One rib down the center from the base to the tip of the leaf.

Leaf habit: Average amount of curl.

Leaf denisty: Slightly less dense than average.

STEM

Stem strength: Very good, better than average.

Stem color: R.H.S. Green Group 139A with a whitish color over the green.

Nodes: Average.

*Space between nodes.*—Approximately 3 inches at midstem.

Stem branching: Very good, not clubby.

BUDS

Bud shape: An elongated oval, rather than a round oval. Very unlike most miniature carnation buds.

Bud color: Top half LCC H-22 L-13 bottom half blends into LCC H-22 L-9.

Average number of flowering buds per stem: 4–5 Mostly 5.

Uniformity of bud opening: Very uniform, all open at about the same time.

Bud splitting: Very seldom.

Number of sepals per calyx: 90% of calyxs hve 5, 10% of calyxs have 6.

FLOWER

Description of the color of the bloom: The bloom is a very vibrant and bright white, R.H.S. White Group 155D. Occasionally, but not very noticeably, there will be a small strip or speck of Hot Pink on a petal, LCC H-41 L-10 top of petal and LCC H-41 L-9 bottom of petal. However the bloom appears white and the pink is not readily noticeable. The bloom is moderately serrated.

General tonality of the clor: Bright, a very vibrant white.

Diameter of average bloom: 2¼ to 2½ inches.

Bloom shape: Generally round with a high center and flat outer petals.

Keeping quality: Average.

Fragrance: Above average, a very strong fragrance.

PETALAGE

Petal texture: Soft and velvety.

Petal edge: Medium serration.

Petal color: White R.H.S. White Group 155D, Hot Pink LCC H-41 L-10.

Color stability: Excellent. No known reversions to Niky yet.

Petal size:

*Average length.*—2 Inches.

*Average width at widest point.*—1 Inch.

Calyx color: Top half LCC H-22 L-13, the bottom half blends into LCC H-22 L-9, the tips of the leaves on the bottom of the calyx are LCC H-19 L-15.

REPRODUCTIVE ORGANS

Stamen: With and without anthers.

Average length of stamen: 1¼ Inches—subtract ⅛ of an inch for a stamen without an anther.

Color of anthers: R.H.S. Gray Yellow Group 161 (D).

Color of filament: R.H.S. White Group 155 (A) but more transparent.

Pistils:

*Shape.*—Approximately 100% have 2 styles.

*Number.*—One.

*Length from tip to ovary.*—⅞ Of an inch.

Stigma:

*Shape.*—Round.

*Color.*—White, it is located at the very tip of the style.

Style:

*Color.*—LCC H-25 L-1.

Ovary:

*Shape.*—Ovid.

*Color.*—Tip LCC H-26 L-8, middle LCC H-22 L-14, bottom LCC H-23 L-2.

*Length.*—⅞ Of an inch.

*Width.*—5/16 Of an inch.

DISTINGUISHING CHARACTERISTICS BETWEEN THE NEW VARIETY AND PARENT

The new variety, Snowflake, is white. The parent variety, Niky, is Hot Pink color. The styles of Snowflake are the same color as the styles of Niky (LCC H-25 L-1) but the styles of Niky have a tinge of Hot Pink (LCC H-42 L-10) on them where the styles of Snowflake don't. The same is true of their filaments. Both varieties' filaments are the same color (R.H.S. White Group 155A) but the filaments of Niky have a tinge of Hot Pink (LCC H-42 L-10) on them where the filaments of Snowflake don't.

SIMILAR CHARACTERISTICS OF THE NEW VARIETY AND PARENT

All of the characteristics of both varieties are similar except for the distinguishing characteristics referred to above.

I claim:

1. A new and distinct variety of miniature carnation plant, substantially as herein shown and described.

* * * * *

PRIOR ART